(12) United States Patent
Rattner

(10) Patent No.: US 6,421,649 B1
(45) Date of Patent: Jul. 16, 2002

(54) MEDICAL SYSTEM ORGANIZED AND OPERATING TO ADJUST FOR DELAYS ASSOCIATED WITH PATIENTS PROCEEDING THROUGH THE SYSTEM

(75) Inventor: Manfred Rattner, Grossenseebach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/313,470

(22) Filed: May 17, 1999

(30) Foreign Application Priority Data

May 15, 1998 (DE) ......................................... 198 22 022

(51) Int. Cl.7 ............................................... G06F 17/60
(52) U.S. Cl. .................................. 705/2; 705/9; 705/100
(58) Field of Search ....................... 705/1, 2, 9; 700/100

(56) References Cited

U.S. PATENT DOCUMENTS

| | | | |
|---|---|---|---|
| 5,065,315 A | * 11/1991 | Garcia | 700/100 |
| 5,634,100 A | * 5/1997 | Capps | 705/9 |
| 5,748,907 A | * 5/1998 | Crane | 705/9 |
| 5,963,913 A | * 10/1999 | Henneuse et al. | 705/9 |
| 6,047,259 A | * 4/2000 | Campbell et al. | 705/2 |
| 6,047,260 A | * 4/2000 | Levinson | 705/9 |

FOREIGN PATENT DOCUMENTS

GB    2 249 851    5/1992

OTHER PUBLICATIONS

Article entitled "Take the Pain out of Patient Scheduling", published in Hospital Practice, Nov. 15, 2000.*
Article entitled "Enterprise Wide Scheduling: Do You Need It", published in Health Mangement Technology, May 1996.*
Article entitled "Rehab Facility Saves $300,000 a yers, Reduces FTE's with Scheduling System", published in Health Management Technology, Jun. 1997.*

\* cited by examiner

*Primary Examiner*—Sam Rimell
(74) *Attorney, Agent, or Firm*—Schiff Hardin & Waite

(57) ABSTRACT

A medical system has a number of data processors which are allocated to medical organizational units of a similar type or of different types, these data processors being connected for data exchange. The medical system is operated such that data related to the medical system concerning time sequences for the flow of material and/or persons between the organizational units can be entered at individual or at all data processing units of the medical system, and can be retrieved immediately by each data processing means of the medical system, so that pre-planned flow sequences can be adjusted, as needed.

4 Claims, 2 Drawing Sheets

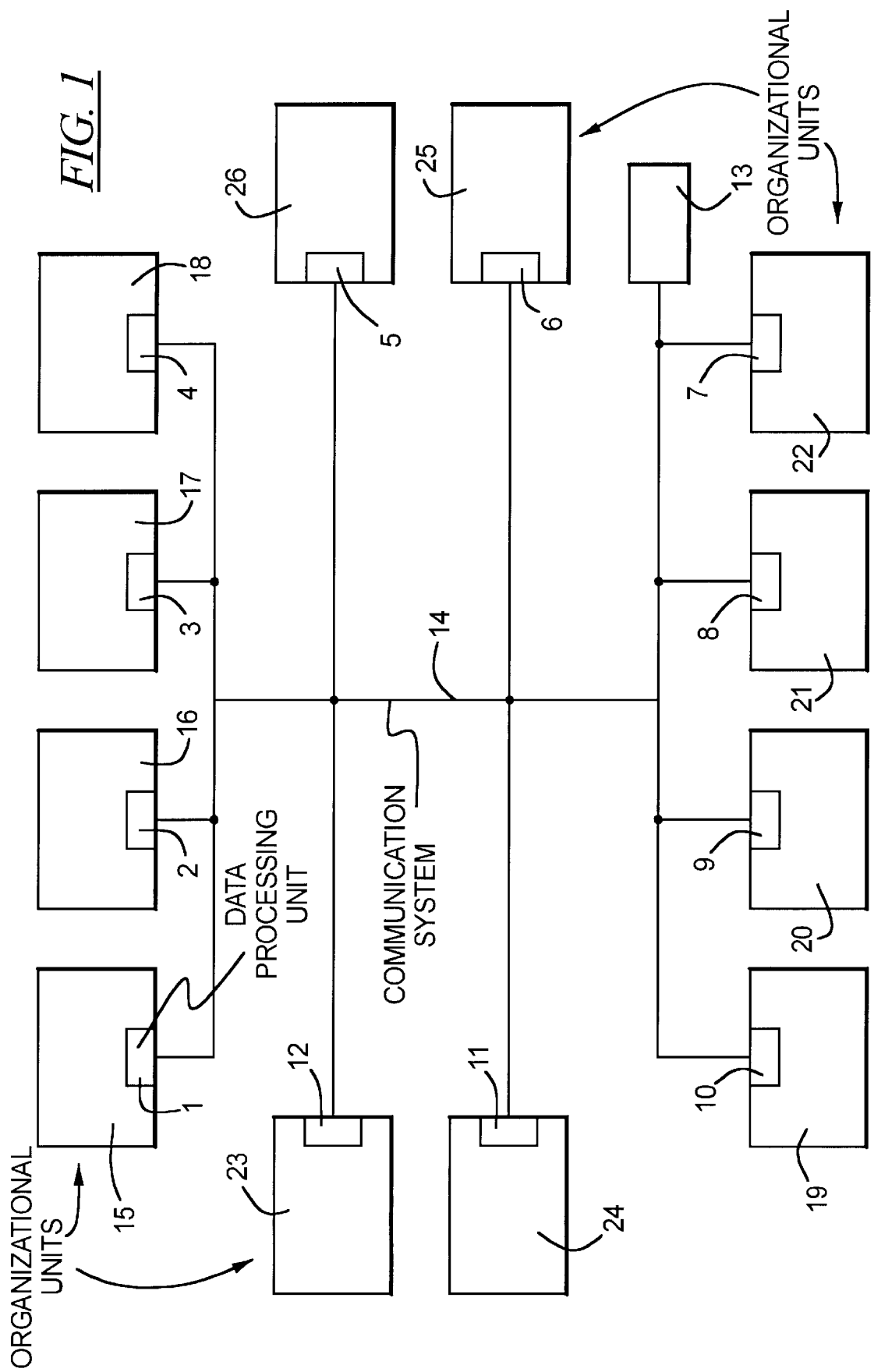

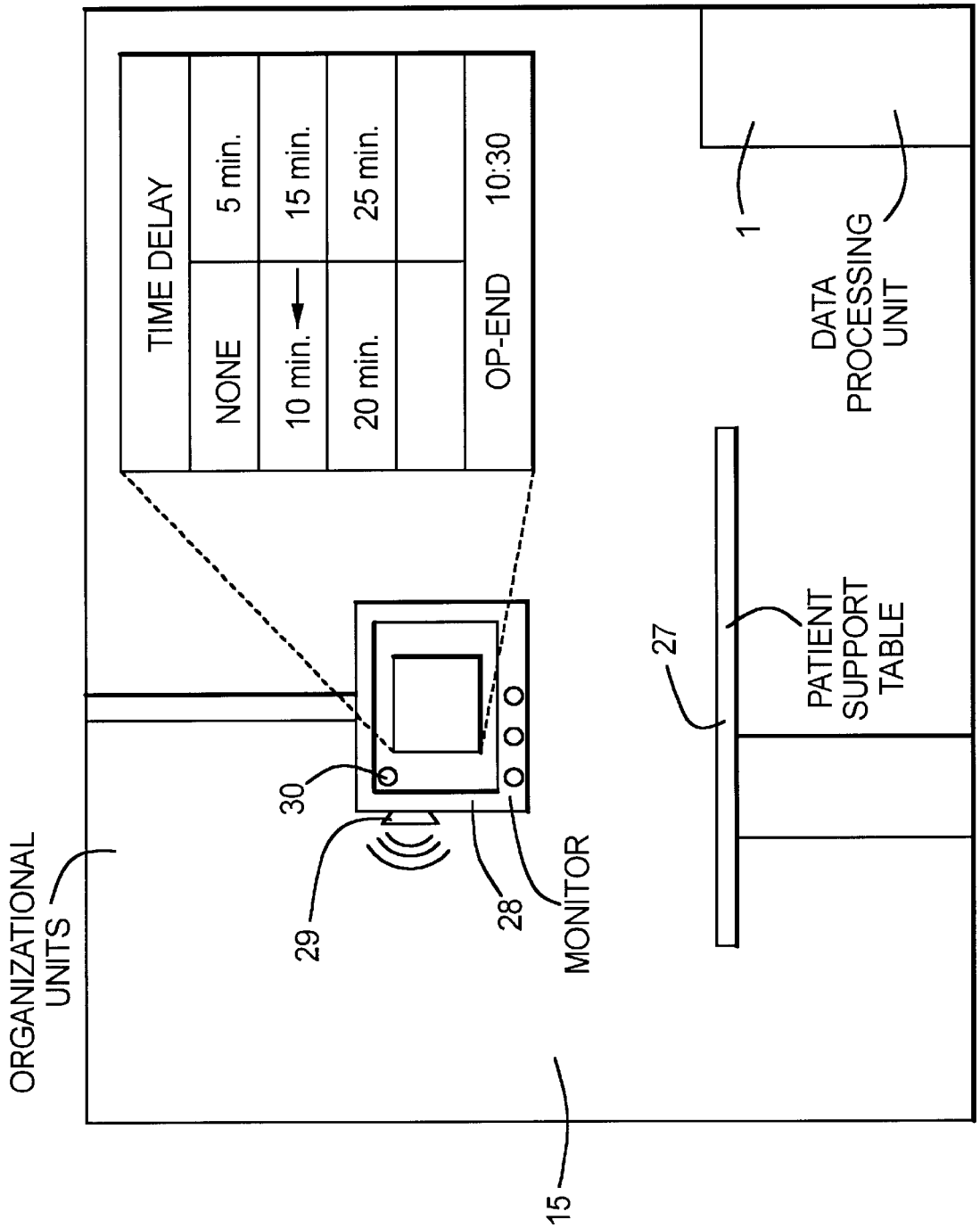

MEDICAL SYSTEM ORGANIZED AND OPERATING TO ADJUST FOR DELAYS ASSOCIATED WITH PATIENTS PROCEEDING THROUGH THE SYSTEM

BACKGROUND OF THE INVENTION

1. Field of the Invention

The present invention relates to a medical system of the type having a number of data processors which are allocated to medical organization units of a similar or varied nature.

2. Description of the Prior Art

Medical facilities such as hospitals or clinics contain different organizational units, such as nursing stations, anesthesia stations, operating rooms, etc., which cooperate in the treatment and care of patients.

German OS 41 32 951 A1 describes a medical facility with a data processor in the form of a central computer and portable terminals which are or can be connected to each other for data exchange. A library of all the patient care measures for the medical facility is stored in the central computer. The portable terminals are provided for the nursing personnel. The terminals can be connected to a data network and can be connected to the central computer via the data network. In this way, the nursing personnel can retrieve instructions for care at the bed of a patient, for example, and can store the measures taken directly on the central computer, thereby reducing the sources of error due to subsequent incomplete or incorrect records.

In the course of a patient's stay in the medical facility, the patient proceeds through all or only a part of the organizational units of the medical facility, depending on the patient's reason for the visit. For example, a patient who needs to undergo a surgical intervention passes through:

a) a nursing station at which the patient is received and at which the patient remains until after the surgical intervention convalescence, b) a patient transport unit which is responsible for conveying the patient between individual organizational units of the clinic, c) different stations for preparatory examinations for the operation, e.g. the radiological station, d) an anesthesia station, at which the patient is prepared for the operation and is anesthetized, and e) an operating room in which the patient undergoes the surgical intervention. To guarantee an effective passage of patients through the individual organizational units, i.e. to ensure the economic efficiency of the medical facility as well, time schedules for the passage of the patient are created which give the planned arrival time and the length of stay of the patient in each organizational unit. The time schedules form the organizational basis of the individual organizational units, e.g. in reference to the use of personnel.

The current practice of creating time schedules has proven to be disadvantageous, however, given the passage of a number of patients through a number of organizational units in one day because if the planned passage of one patient through an organizational unit of the medical system is delayed, the sequence of other organizational units which need to accept the patient or to transfer a different patient to the blocked organizational unit is also delayed. Since the flow of information between the organizational units is frequently insufficient, the organizational units may not be able to promptly adjust to the successive delays in the planned time sequences and as a result the personnel of the organizational units my not be utilized effectively, necessitating the postponement or even cancellation of actual planned events, such as a patient's operation, despite preparatory measures for the operation having already been carried out at the patient.

Given these types of time delays, the planned time sequences of individual organizational units can become so confused that the effectiveness of the organizational units suffers, which can be associated with economic disadvantages for the medical facility.

SUMMARY OF THE INVENTION

It is thus an object of the present invention to provide a medical system of the type described above wherein the economic efficiency of a medical facility formed of organizational units is increased.

This object is inventively achieved in a medical system with a number of data processors which are allocated to organizational units of the same type and/or of different types, the data processors of which are connected to each other for data exchange, the medical system operating such that the data relating to the medical system concerning time sequences for the flow of material and/or persons between the organizational units can be entered to one or more individual data processors of the medical system, or to all the data processors of the medical system, and can be retrieved directly by the data processors of the medical system. This guarantees that each organizational unit can virtually immediately report delays as may arise in planned time sequences in the passage of patients or material to the operational units which directly cooperate with the organizational unit once the occurrence of a delay is certain. To this end, the medical system is operated to allow the input of a time delay to all or to only individual data processors of the medical system which are allocated to organizational units that are particularly susceptible to delays, such as operating rooms, as warranted, and this input of delay can be immediately retrieved by every data processor. Thus, current information about the time sequences of the medical system is always available to the individual organizational units of the medical system, so that the organizational units can adapt their internal sequence accordingly. In this way, the loss of time due to unnecessary waiting and the associated tie-up of personnel of an organizational unit and the premature undertaking of preparatory measures can be avoided, so that the economic efficiency of medical facilities formed of these types of cooperating organizational units can be increased.

In an embodiment of the invention the medical system has a control computer which overrides the data processors and which processes the data entered at the individual data processors and makes this data available to all the data processors. The control computer can be a central computer of the medical system, but it is also possible for one of the data processors of the organizational units to constitute the overriding control computer for the medical system. In this variation, an additional overriding control computer could be forgone.

According to a preferred embodiment of the invention, the control computer interrogates individual or all data processors of the organizational units as to whether the predetermined time sequences can be maintained; it processes any delay times for the flow of material and/or personnel, these times having been entered, as warranted, at individual data processors of the medical system; it updates the time sequences; and it makes the updated time sequences immediately available to the data processors of the medical system. Thus, it is not left up to the personnel of an organizational unit to think of corresponding delay reports and messages to other organizational units. Rather, for updating the time sequences, the control computer of the medical system advantageously requests the data from the organizational units itself.

In another variant of the invention the control computer interrogates the data processors of the organizational units as to the maintenance of the time sequences in cycles. In this way, the time sequences for the flow of material and/or persons is checked at defined intervals, so it can be assumed that in the corresponding cycle time, the retrievable data of the medical system are always current.

According to a further variant of the invention, prior to the chronological arrival of a planned event of an organizational unit, the control computer transmits a control message to the data processor of that organizational unit, which prompts that data processor to deliver an optical and/or acoustical signal as an indication of the arrival time of the event. Thus, the organizational units are notified in advance of the impending occurrence (arrival) of an event, so that a preparatory action which should be carried out is not forgotten through oversight. This presents another possibility to notify the control computer if a time delay exists.

According to another embodiment of the invention, the medical facility is a surgical facility in which the organizational units include operating rooms and/or nursing stations and/or anesthesia stations and/or patient transport units and/or material management units of medical material.

BRIEF DESCRIPTION OF THE DRAWINGS

FIG. 1 is a block diagram of a medical system with data processing units which are allocated to medical organizational units in accordance with the invention.

FIG. 2 is a schematic illustration for an organizational unit of FIG. 1.

DESCRIPTION OF THE PREFERRED EMBODIMENTS

FIG. 1 depicts a medical system with data processing units 1 to 13, which are connected to one another via a communication system 14 and which thus can exchange data with one another. In the exemplary embodiment, the data processing units 1 to 13 are conventional computers such as PC's, and the communication system 14 is a communication bus such as a CAN bus.

The data processing units 1 to 12 are allocated respectively to medical organizational units of a medical facility, these organizational units being autonomous, but cooperating within the medical facility. In the exemplary embodiment, the medical facility is the surgery facility of a clinic. As organizational units, the surgery facility includes operating rooms 15 to 18, nursing stations 19 to 22, anesthesia stations 23, 24, a patient transport unit 25 and a material management unit 26 for medical material.

In the exemplary embodiment the data processing unit 13, which is not allocated to any organizational unit, is a control computer of the medical system. This type of control computer 13 need not be present, however. Instead, one of the data processing units 1 to 12 of the medical organizational units can take over the duty of a control computer for the medical system. Via the control computer 13, the medical system can be operated such that the data related to the medical system concerning time sequences for the flow of persons, i.e. the transfer of patients from one organizational unit to another organizational unit of the medical facility, and the flow of material, i.e. the transfer of medical material from the material management unit 26 to one of the other organizational units 15 to 25, can, in the exemplary embodiment, be entered at each data processing unit 1 to 12 of the medical system and can be immediately retrieved by each data processing unit 1 to 12, subsequent to transmission to the control computer 13 via the communication system 14 and processing and updating by the control computer 13. This is of particular importance when this input relates to the chronological, and thus economical, optimization of the flow of persons and material between the organizational units 15 to 26.

For patient surgeries in the surgery facility there is an operating plan for each day, in which it is stated for which patient surgery conducted is in each operating room, and at what time, and how long each operation is to last. Accordingly, for the nursing stations at which the patients are received, there are time specifications stating when each patient must be ready for the operation and when each patient must be transferred to the patient transport unit 25. Furthermore, the arrival or reception times and length of stay of a patient in the patient transport unit 25 prior to moving to the anesthesia stations 23, 24 at which the patients are anesthetized are specified. It is also specified when the medical material which is needed for the operations to be performed must be made available, by the material management unit 26, in the operating rooms which are provided for the operations.

To optimize these complex time sequences which are covered in the operating plan, the current time sequences are made available to all data processing units 1 to 12 of the organizational units 15 to 26 of the surgery via the control computer, so that the personnel of the organizational units 15 to 26 can continuously retrieve whether the original time specifications still apply. For example, if an operation in operating room 15 is extended, and the subsequent operation in the operating room 15 is postponed a certain amount of time, then the surgeon working in the operating room 15 can enter this information via the data processing unit 1 of the operating room 15, this surgeon having access to the data processing unit without becoming unsterilized, in a manner which is not illustrated. The surgeon thus has the opportunity to inform other organizational units with respect to the length of the operation from a sterile environment. The control computer 13 registers this change, updates the time sequences and makes the updated time sequences immediately available to all data processing units 1 to 12 subsequent to the updating, so that the personnel of the organizational unit that is connected downstream to the organizational unit of the operating room 15, namely the nursing station, and the organizational unit upstream, namely the anesthesia station, can retrieve the time delay via the control computer 13 and can initiate any preparatory measures later than originally planned. In this way, the wait time for personnel in the organizational units can be reduced and thus the economic efficiency of the medical facility can be increased.

In the exemplary embodiment, the control computer 13 interrogates the organizational units 15 to 23 of the surgery facility, in cycles, as to whether the existing time sequence for the passage of patients and/or material can be maintained. FIG. 2 illustrates an example of such an interrogation for the operating room 15. In FIG. 2, the operating room 15 is illustrated only in an extremely simplified form, with only a patient support table 27, the data processing unit 1 of the operating room 15, and a monitor 28 which is allocated to the data processing unit 1 and which is connected to it via connecting cables (not illustrated). On the monitor 28, the query regarding the time delay appears in cyclical intervals. Using a known input means (such as a joystick, a mouse or a keyboard), which are allocated to the data processing unit 1, the operating surgeon (not illustrated), or other personnel of the operating room 15 on instructions from the surgeon, produce an input indicating whether there is a time delay, and if so to what extent a time delay must be accounted for, in the sterile environment. The input means have been sterilized so that the surgeon or the personnel do not become unsterilized in making this input. If, for example, the surgeon indicates that a time delay of about 10 minutes is to be expected, as is illustrated by an arrow in the case of the exemplary embodiment, then the control computer 13 registers this entry, updates the time sequences for the surgery, and makes the updated time sequences for the surgery immediately available to the data processing units 1 to 12 of the organizational units 15 to 26 of the surgery. In this way, the updated time sequences are available to each are available to each organizational unit 15 to 26, so that events or preparatory measures to be initiated can be initiated later, according to the time delay.

To prevent the personnel of the organizational units from having to constantly monitor the time sequences as to whether time delays have occurred, the control computer 13 transmits a control command to the data processing unit of an organizational unit prior to the planned or detected arrival of an event at that organizational unit, this command prompting the data processing unit of that organizational unit to deliver an optical and/or acoustical signal as an indication of the impending arrival of the event. In the case of the operating room 15 illustrated in FIG. 2, a speaker 29 which is allocated to the data processing unit 1 is arranged at the monitor 28 for this purpose, or an optical signal in the form of a blinking circle 30 can be faded into the monitor image of the monitor 28. In this way, the surgeon working in the operating room 15 can be notified that the planned end of an operation is imminent by means of an acoustical and/or optical signal.

Instead of a blinking circle 30, a window can be faded into the monitor 28 which indicates the end of the operation. If the data processing unit has an acoustical transducer already built into or connected to it, then there is no need for an additional component such as the speaker 29 as well.

Analogously to the described course of action, corresponding control commands can also be transmitted to other data processing unit of the surgery facility; for example, to the patient transport 25 unit as a request to transfer a patient from a nursing station to an anesthesia station 23, 24.

The inventive medical system has been detailed above in the example of a surgical facility. The use of the medical system is not limited to surgical facilities, however.

The above described embodiment should be understood as exemplary only, it being possible for the medical facility to have additional or different organizational units than those described here.

It is not necessary to allow time delays to be entered at all data processing units of the medical system, but only at data processing units of organizational units that are particularly susceptible to time delays, such as operating rooms.

Likewise, not all data processing units of the medical system must be interrogated for time delays. It is also possible for only those data processing means to be interrogated which are allocated to organizational units which are particularly susceptible to time delays.

Although other modifications and changes may be suggested by those skilled in the art, it is the intention of the inventor to embody within the patent warranted hereon all changes and modifications as reasonably and properly come within the scope of their contribution to the art.

I claim as my invention:

1. A medical system comprising:

a plurality of organizational units adapted for respectively performing procedures, at respective predetermined times, in a predetermined sequence of procedures relating to a treatment of a patent;

a plurality of data processing units respectively associated with said organizational units;

a communication network connecting all of said data processing units for data exchange therebetween;

at least one of said data processing units having an input unit allowing entry of an input of a time increment delay which effects the respective times at which the respective procedures in at least some of the other organizational units in said predetermined sequence, said time increment delay input being immediately retrieved by the respective data processing units via said communication network; and a control computer, connected to said communication network, which overrides all of said data processing units receiving and processing said time increment delay input, said control computer producing processed information relating to said time increment delay and immediately making said processed information available to all of said data processing units via said communication network, said control computer interrogates at least some of said data processing units as to whether said predetermined sequence can be maintained, and processing any time increment delays entered via the respective data processing units and adjusts said predetermined sequence dependent on said time increment delays to produce an updated sequence, and said control computer makes said updated sequence immediately available to all of said data processing units via said communication network.

2. A medical system as claimed in claim 1, wherein said control computer cyclically interrogates said data processing units as to whether said predetermined time sequence can be maintained.

3. A medical system as claimed in claim 1, wherein said control computer transmits a control command to respective data processing units of respective organizational units prior to an occurrence of a procedure at the respective organizational unit in said predetermined sequence, said control command prompting the data processing unit which receives said control command to emit a humanly perceptible signal as an indication of said occurrence of said procedure.

4. A medical system as claimed in claim 1, wherein said organizational units comprise units selecting from the group consisting of operating rooms, nursing stations, and anesthesia stations, patient transport units, and medical material management units.

* * * * *